United States Patent [19]

Minoha et al.

[11] Patent Number: 5,139,829
[45] Date of Patent: Aug. 18, 1992

[54] METHOD FOR PRODUCING OXYGEN DETECTION ELEMENT

[75] Inventors: Ken Minoha, Aichi; Haruhisa Shiomi, Kyoto; Yoshitake Kawachi, Aichi, all of Japan

[73] Assignee: NGK Spark Plug Co., Ltd., Aichi, Japan

[21] Appl. No.: 727,361

[22] Filed: Jul. 9, 1991

Related U.S. Application Data

[63] Continuation of Ser. No. 444,907, Dec. 4, 1989, abandoned.

[30] Foreign Application Priority Data

Dec. 22, 1988 [JP] Japan .............................. 63-323966
Jan. 18, 1989 [JP] Japan .............................. 1-10199
Jan. 18, 1989 [JP] Japan .............................. 1-10200

[51] Int. Cl.$^5$ ............................................. C23C 26/00
[52] U.S. Cl. ..................................... 427/123; 427/125; 427/126.1; 427/126.3; 427/126.4; 427/191; 427/372.2; 427/376.2; 427/376.3
[58] Field of Search ............ 427/123, 125, 191, 126.3, 427/126.1, 126.4, 372.2, 376.2, 376.3

[56] References Cited

U.S. PATENT DOCUMENTS

| | | |
|---|---|---|
| 3,617,358 | 11/1971 | Dittrich . |
| 3,640,757 | 2/1972 | Grubba . |
| 3,663,280 | 5/1972 | Lee ....................... 426/125 |
| 3,935,089 | 1/1976 | Togawa et al. ............ 204/195 |
| 3,978,006 | 8/1976 | Topp et al. ............... 252/195 |
| 4,021,326 | 5/1977 | Pollner et al. ............ 204/195 |
| 4,049,532 | 9/1977 | Clerbois ................ 427/123 |
| 4,107,018 | 8/1978 | Bode ..................... 427/123 |
| 4,170,530 | 10/1979 | Watanabe ............... 427/126.3 |
| 4,170,531 | 10/1979 | Watanabe et al. ........ 204/195 |
| 4,208,265 | 6/1980 | Hori ...................... 427/123 |
| 4,272,349 | 6/1981 | Furutani et al. .......... 204/195 |
| 4,280,890 | 7/1981 | Friese et al. ............. 204/195 |
| 4,284,486 | 8/1981 | Shinohara ............... 427/123 |
| 4,296,148 | 10/1981 | Friese .................... 427/123 |
| 4,297,192 | 10/1981 | Shinohara et al. ........ 204/195 |
| 4,655,892 | 4/1987 | Satta ..................... 427/125 |

FOREIGN PATENT DOCUMENTS 731596 4/1966 Canada ............................ 427/123

Primary Examiner—Shrive Beck
Assistant Examiner—Vi Duong Dang
Attorney, Agent, or Firm—Sughrue, Mion, Zinn Macpeak & Seas

[57] ABSTRACT

A method for producing an oxygen detection element having uniform pores and an excellent durability against toxic matter contained in the measurement gas. The method includes a first step of applying a paste to be sintered to form a catalytic electrode layer onto at least a part of an oxygen-ion conductive solid-state electrolytic body, and sintering the paste to thereby form said catalytic electrode layer at a predetermined position on said surface of said solid-state electrolytic body after sintering, and a second step of forming an electrode protection layer for coating and protecting at least a part of the catalytic electrode layer either after or simultaneous with the first step. In a first embodiment, the paste contains mainly a noble metal powder acting as a catalyst and an organic metal compound, in a second embodiment mainly co-precipitated powder consisting of a noble metal and a metal hydroxide, and in a third embodiment mainly noble metal powder and a powder of a metal other than a noble metal.

39 Claims, 2 Drawing Sheets

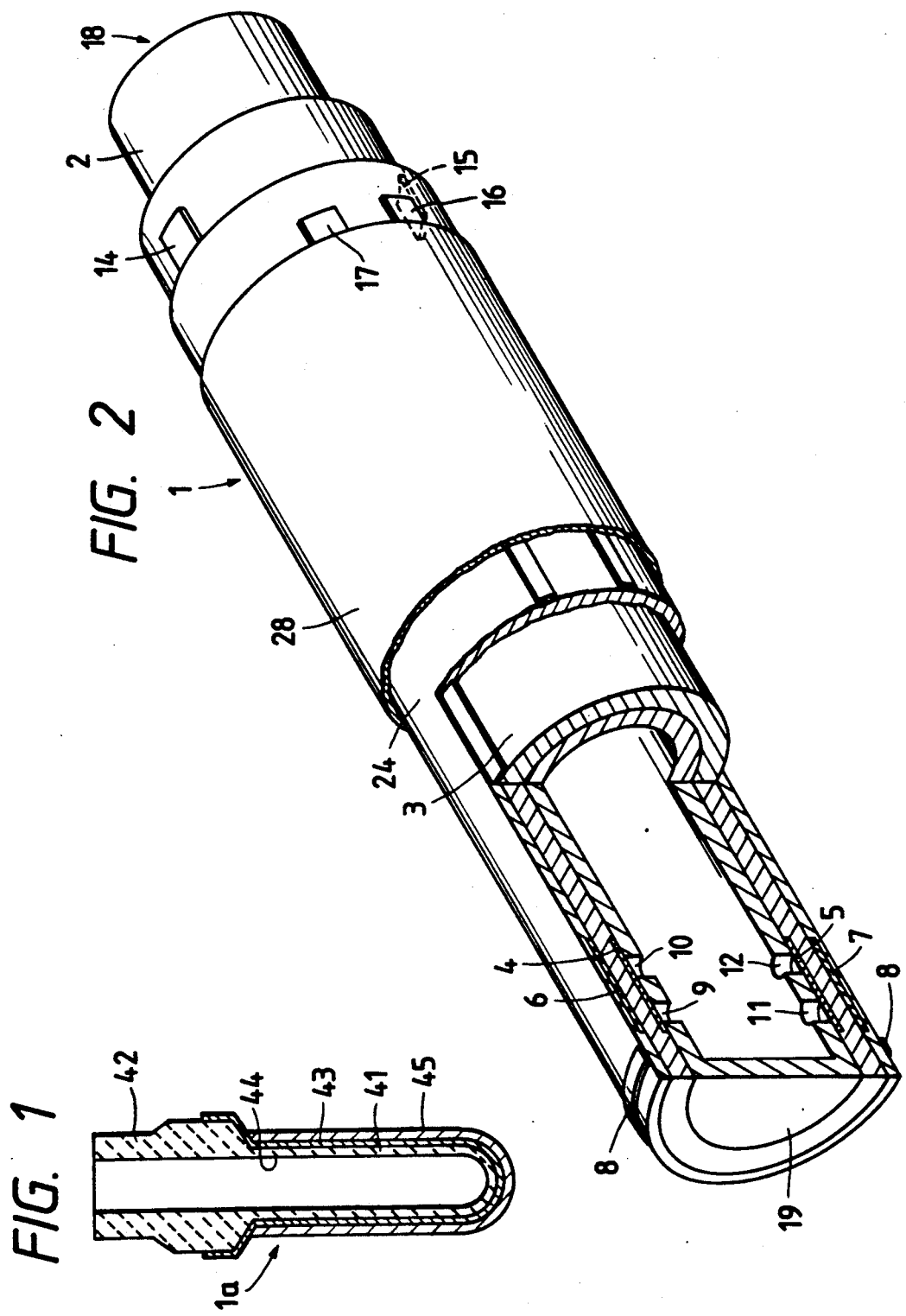

METHOD FOR PRODUCING OXYGEN DETECTION ELEMENT

This is a Continuation of application Ser. No. 07/444,907 filed Dec. 4, 1989 now abandoned.

BACKGROUND OF THE INVENTION

The present invention relates to a method for producing an oxygen detection element, and, more particularly, to a method for producing an oxygen detection element having an excellent durability against toxic matter in the measurement gas brought about by providing the detection element with electrodes having uniform pores. The present invention is applied to oxygen detection elements for measuring oxygen concentration in exhaust gases from internal engines, various kinds of combustors, and the like. More particularly, the present invention is applicable to zirconia lambda sensors, zirconia air-fuel ratio sensors, and the like.

A conventional method for producing an oxygen detection element includes steps of: preparing an unsintered oxygen-ion conductive solid-state electrolytic body; applying a paste containing a fine powder-like ceramic material, a fine powder-like catalytic material for effecting gas equilibrium, and diluent oil onto at least one portion of the outer surface of the solid-state electrolytic body; sintering the body having the paste thereon to produce an electrode on the solid-state electrolytic body in the form of a catalytic layer having pores; and forming an outer protective layer covering the electrode. (See, for example, Japanese Patent Publication No. 59-24382.) The element produced by this method exhibits an abrupt change in output voltage as the stoichiometric ratio of the measurement gas is crossed.

However, the main components for forming the electrode by the conventional method include noble metal fine particles and ceramic fine particles. Accordingly, a large amount of ceramic material (for example, five times or more than the amount of the catalytic material) must be added to the catalytic material to bring the particles sufficiently into contact with each other to thereby prevent self sintering of the catalytic material and to form electrodes having pores. In this case, the electrical conductivity of the electrodes is apt to be reduced. Further, the contact area between the solid-state electrolyte and the catalytic material forming the electrode on the surface of the solid-state electrolyte is apt to be reduced. Thus, there arises a problem in that the .intern 1 resistance of the electrode increases, making it necessary to increase the thickness of the coating of catalytic material.

Furthermore, since the aforementioned two kinds of powder are made of different materials, for example, noble metal and ceramics, it is difficult to mix them uniformly. Even if they are mixed sufficiently, a portion which has an insufficient dispersion of ceramic powder may remain because of the acidity or alkalinity of the ceramic powder (depending on the kind of solvent used), as a result of which a nonuniform microscopic structure is apt to be formed. Accordingly, pores can be formed which are so large that gas directly reaches the three-phase boundary between the electrode and the solid-state electrolyte.

As described above, reducing the contact area brings about a reduction of the three-phase boundary, and, at the same time, the large pores result in direct contact by the gas. Accordingly, when the oxygen detection element is used in a gas containing toxic matter such as silicon, sulfur, lead or the like, the toxic matter may bring cause an abnormality in the characteristics of the sensor in a short time.

Further, there is a difference in melting point among the materials of which the paste is formed. Zirconium oxide (generally used in the solid-state electrolyte) or aluminum oxide (present as an impurity) has a higher melting point than that of platinum, rhodium, palladium or the like. Thus, self-sintering of the noble metal powder occurs if a sufficient quantity of noble metal powder is not added.

Therefore, an electrode formed by applying and sintering a paste prepared as a mixture of powdered materials is not satisfactory in practical use.

SUMMARY OF THE INVENTION

Overcoming the problems described above, the present invention provides a method for producing an oxygen detection element excellent in durability against toxic matter and which has electrodes having uniform pores which are formed efficiently and easily by the use of paste containing noble metal powder and an organic metal compound, paste containing co-precipitated powder consisting of noble metal and metal hydroxide, or paste containing noble metal powder and metal powder other than noble metal.

BRIEF DESCRIPTION OF THE DRAWINGS

FIG. 1 is a longitudinal sectional view of an oxygen detection element which relates to Examples 1, 2 and 3 herein;

FIG. 2 is a partly broken perspective view of an oxygen detection element which relates to Examples 4, 5 and 6 herein.

DESCRIPTION OF THE PREFERRED EMBODIMENTS

Figure 3:
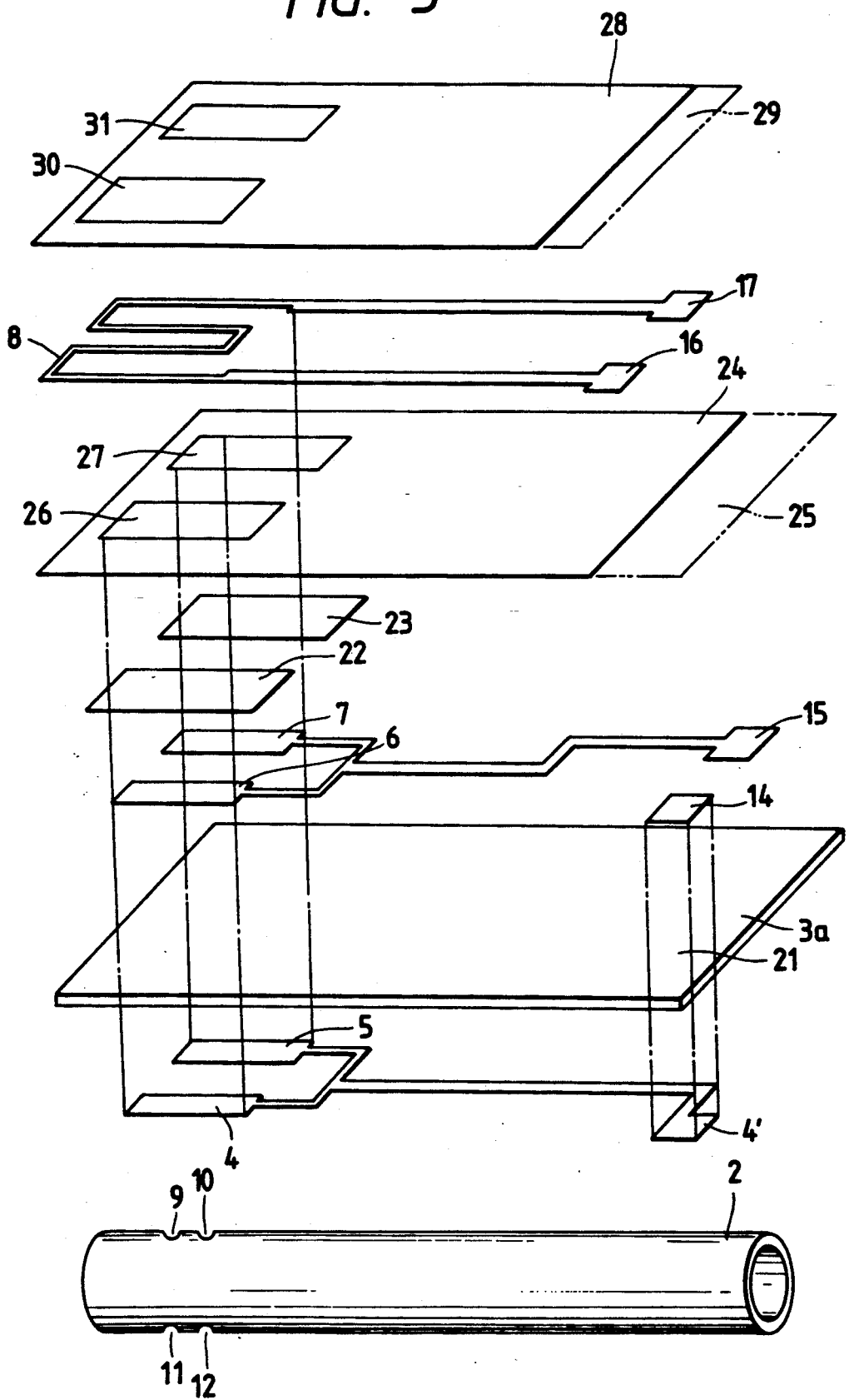
FIG. 3 is an exploded perspective view of the element depicted in FIG. 2.

The method for producing an oxygen detection element according to the present invention comprises: a first step of applying paste to be sintered to form a catalytic electrode layer onto at least a part of an oxygen-ion conductive solid-state electrolytic body, which may or may not yet be sintered, and sintering the paste to thereby form the catalytic electrode layer at a predetermined position on the surface of the solid-state electrolytic body; and a second step of forming an electrode protection layer for coating and protecting at least a part of the catalytic electrode layer after the first step or simultaneously with the first step; in which the first step includes the steps of applying paste mainly containing noble metal powder acting as catalyst and an organic metal compound, or paste mainly containing co-precipitated powder consisting of noble metal and metal hydroxide, or paste mainly containing noble metal powder and powder of metal other than noble metal and inclusive of alloy onto the oxygen-ion conductive solid-state electrolytic body, and then sintering the paste.

The shape of the element as a whole may be a one-end-closed cylindrical form (hereinafter merely called a "cylindrical form"), or it may be a flat form.

The aforementioned solid-state electrolytic body has oxygen-ion conductivity. For example, stabilized zirconia, such as $ZrO_2$-$Y_2O_3$, $ZrO_2$-$CaO$ or the like may be used as the material of the electrolytic body. The thickness of the electrolytic body is not limited specifically. For example, the body may be either relatively thick or relatively thin.

With respect to the relation between the above-mentioned first and second steps, the electrode protection layer may be formed after formation of the catalytic electrode layer by sintering in the first step. In this case, the solid-state electrolytic body may be in either a sintered or unsintered state. When an unsintered solid-state electrolytic body is used, the body is sintered at the same time the paste layer is sintered to prepare the catalytic electrode layer. Further, the paste to be formed into the electrode protection layer is applied, and then the paste and material are sintered integrally at the same time to thereby form the catalytic electrode layer and the electrode protection layer at the same time. In this case, if an unsintered solid-state electrolytic body is used, the unsintered solid-state electrolytic body is sintered simultaneously with the sintering of the paste and material.

The organic metal compound may be a compound having direct binding of metal and carbon, or it may be a compound having binding of metal and O, N or the like. Otherwise, the organic metal compound may be a compound having both the aforementioned binding forms. "Organic metal compound" as used herein means a compound containing an organic group, the whole compound being soluble in a predetermined organic solvent. In short, a wide definition is applied to the term "organic metal compound". Elements capable of being directly bound to the metal are variously suitably selected corresponding to factors such as the kind of the metal, the kind of the organic group, and the stability of the compound. In general, the organic metal compound is changed to a predetermined metal oxide and the like by heat decomposition. Metal alkoxide or the like is generally used as the compound. This is because metal alkoxide is capable of being easily dissolved in general organic solvent, easily producing oxide by heat decomposition, and it is easily prepared and relatively stable against humidity and the like. In particular, when the alkyl group becomes larger than butyl, the compound is improved in solubility, stability against humidity and the like, and ease of handling. Accordingly, the size of the alkyl group is selected corresponding to purpose. In this case, it may be preferable, according to the purpose of use, that the organic metal compound be provided in solution. Further, the organic metal compound may contain other halogens, other elements, other organic atomic groups, or the like.

The word "co-precipitate" relates to the fact that powder or the like containing at least two compounds is produced by simultaneous precipitation of the compounds from a solution in which at least two compounds coexist. In the present invention, when a mixture solution of a compound containing a precious metal element and a compound containing other metal element is subjected to precipitation in a reducing atmosphere, co-precipitated powder of noble metal and metal hydroxide is produced. In this case, the solution is generally an aqueous solution but is not limited thereto. For example, the solution may be a solution prepared with an organic solvent or may it be a solution prepared by mixing the two.

The compounds used herein are selected suitably so that they can be dissolved in solvent and can be co-precipitated under predetermined conditions. In general, suitable compounds include nitrates, sulfates, chlorides or the like. In the case where organic solvent is used, the compounds may be organic metal compounds. Further, the conditions of co-precipitation are variously suitably selected corresponding to the actual compounds used and other factors. Examples of these conditions are a condition that alkali, ammonia or the like is added, a condition that a great deal of water is added to perform hydrolyzation, a condition that organic solvent is added, and a condition that heating is made if necessary. Similarly, the kind and condition of the reducing agent can be suitably selected corresponding to the kind of the compound to be reduced.

The words "metal hydroxide" used herein means a compound having a hydroxide group. The compound is changed to oxide by sintering in the later step. The words "noble metal" means a metal element having catalytic activity. Examples of the noble metal are Ag, Au and the platinic metals (Ru, Os, Rh, Ir, Pd and Pt). One noble metal may be used or two or more may be used.

The "metal other than a noble metal" is changed to oxide as a ceramic component by sintering in the later step. Examples of the metal of the organic metal compound, the metal hydroxide, or the metal powder other than a noble metal are elements except elements such as Pb, Zn, Cd, Sn, Hg, and the like which are not suitable since they react with the catalytic metal such as platinum to suppress the catalytic action thereof. Typical examples of suitable elements are Li, Na, K, Be, Mg, Ca, Sr, B, Al, Ga, Si, Ge, Sb, Bi, Ti, Zr, V, Y and the like. In particular, Mg, Al, Zr, Ca, Sr, Ti or Y are preferred because those elements do not suppress the catalytic action, the elements are changed to stable oxide after heat decomposition, the elements produce on excellent sintered body, and they are inexpensive. Because Si tends to reduce the catalytic action of Pt or the like, it is undesirable to employ a large quantity of Si. However, a small quantity of Si may be added in order to control the overall sintering properties of the electrodes.

The aforementioned metal may be a mono-metal consisting of one metal or an alloy of two or more metals. Also, two or more kinds of mono-metals or alloys may be mixed.

Further, two or more kinds of the aforementioned elements may be contained in one organic metal compound, or two or more kinds of organic compounds of the aforementioned metals may be mixed.

Still further, two or more kinds of the aforementioned elements may be contained in one metal hydroxide, or two or more kinds of metal hydroxides of the aforementioned metals may be mixed. Because the compounds are co-precipitated from solution according to the present invention, the uniform dispersion of the respective compounds is excellent even in the latter case.

Predetermined solvents, resin binding agents, low melting point solvent (such as xylene, acetone, and the like) which accelerates dissolution, etc., other than noble metal powder, organic metal compound, co-precipitated powder or the aforementioned two kinds of metal powder, may be used in the paste to form the catalytic electrode layer.

The electrode layer is generally composed of noble metal, such as platinum or the like, and ceramics. The ceramic component is generally in an amount of about 0.5 to about 30 mol % relative to platinum. This is because the thickness of the electrode layer must be increased in the case where the ceramic component is too great, and a problem occurs in gas permeability in the case where the amount of the ceramic component is too little. In the case of the ceramic fine powder used in the prior art approach, 20 to 30 mol % of ceramic must be added to platinum. On the other hand, in the present invention, the quantity of ceramics can be reduced generally to a range of 0.5 to 15 mol %. More preferably, the quantity is 1.5 to 7.5 mol %. As described above, the present invention provides an oxygen detection element excellent in gas permeability although the quantity of ceramic mixture is small compared with the prior art. In short, the catalytic layer can be constructed so that only a necessary portion for detecting the oxygen concentration in the measurement gas has gas permeability.

The following examples serve to illustrate the present invention more in detail.

(1) Production of Elements as Related to Examples 1, 2 and 3 and Comparative Examples 1, 2 and 3

The oxygen detection element 1a of each of Examples 1, 2 and 3 is shown in vertical section in FIG. 1. This element 1a is opened at one end and closed at the other end. The element 1a is constituted by a cylindrical solid-state electrolytic body having a flange portion 42 at the open-end side, a catalytic electrode layer 43 formed on the body to cover almost the whole outer surface of the body, a porous protection layer 45 formed on the layer 43 to cover almost the whole surface of the layer 43, and an inner electrode layer 44 formed on the inside of the cylindrical body. The solid-state electrolytic body is made of zirconia partially stabilized by $Y_2O_3$. The catalytic electrode layer 43 and the inner electrode layer 44 are made of platina-zirconia. The porous protection layer 45 is made of spinel of alumina-magnesia.

EXAMPLE 1

This element was produced by the following method:

Paste to be formed into the aforementioned electrode layers was prepared as follows. Fifteen grams of platinum, zirconium butylate $Zr(OC_4H_9)_4$ (5 mol % relative to platinum), and ethylcellulose resin (5 wt% relative to platinum) were mixed. Butylcarbinol as a solvent was added to the mixture until the viscosity of the resulting mixture became suitable for application. The mixture was milled to prepare a paste. To accelerate the solution of ethylcellulose as a resin binding agent, xylene, acetone or the like may be added to the mixture.

The paste was applied both on the measurement-gas-side outer surface of the as-yet unsintered cylindrical solid-state electrolytic body and on the reference-gas-side inner surface thereof, and then sintered to prepared a sintered solid-state electrolytic body 41 and two electrode layers 43 and 44. Otherwise, the inner electrode layer 44 may be formed on the surface of the sintered solid-state electrolytic body by a known electroless method.

Further, plasma spraying of alumina-magnesia spinel powder onto the surface of the catalytic electrode layer 43 was carried out by a known method to form a porous protection layer 45 for protecting the electrode against the measurement gas. Thus, the element 1a was produced. The protection layer 45 can be formed at any time after the catalytic electrode layer 43 is formed.

The element according to comparative Example 1 was produced in the same manner as described above, except that zirconium butylate used in the paste was replaced by zirconium oxide powder.

EXAMPLE 2

An aqueous solution of chloroplatinic acid ($H_2PtCl_6$) and zirconium oxychloride ($ZrOCl_2$) was prepared. Then, a reducing agent, such as hydrazine or the like was added, together with an alkaline solution or aqueous ammonia, to the aqueous solution and stirred so that co-precipitated powder of Pt and zirconia hydrate was prepared by interaction. The powder was removed, washed with water, and dried. If desired, the co-precipitated powder may be used in the paste without drying. In the case where a pretreatment is required, such as drying the co-precipitated powder and reacting it with Pt without oxidizing the zirconia hydrate contained in the co-precipitated powder, the powder may be treated with heat in a vacuum or in a reducing atmosphere. The powder contains 5% by weight of Zr, the remainder being Pt. Examples of platinic acids which may be used are chloroplatinic acid ($H_2PtCl_6$), sodium chloroplatinate, etc. Examples of suitable Zr compounds are zirconium (IV) nitrate, zirconium (IV) sulfate, etc. Examples of other reducing agents which may be used are formaldehyde, sodium formate (particularly used against sodium chloroplatinate), etc.

Using the co-precipitated powder, the paste to form the aforementioned electrode layers was prepared as follows. Fifteen grams of the powder and 0.7 g of ethylcellulose (5 wt% to platinum) as a resin were mixed. Then, butylcarbidol as a solvent was added to the mixture until the viscosity of the resulting mixture became suitable for application. The mixture was milled to prepare a paste. To accelerate the solution of ethylcellulose as a resin binding agent, xylene, acetone or the like may be added to the mixture.

Then, the paste was applied both on the measurement-gas-side outer surface of the as-yet unsintered cylindrical solid-state electrolytic body and on the reference-gas-side inner surface thereof, and then sintered to prepare a sintered solid-state electrolytic body 41 and two electrode layers 43 and 44. Otherwise, the inner electrode layer 44 may be formed on the surface of the sintered solid-state electrolytic body by a known electroless method.

Further, plasma spraying of alumina-magnesia spinel powder onto the surface of the catalytic electrode layer 43 was carried out by a known method to form a porous protection layer 45 for protecting the electrode against the measurement gas. Thus, the element 1a was produced. The protection layer 45 can be formed at any time after the catalytic electrode layer 43 is formed.

The element according to comparative Example 2 was produced in the same manner as described above, except that the co-precipitated powder used in the paste was replaced by Pt powder and zirconium dioxide powder.

EXAMPLE 3

This element was produced by the following method:

The paste used to form the aforementioned electrode layers was prepared as follows. Fifteen grams of Pt powder (about 1 μm in average diameter), 0.55 g of Zr powder (about 0.5 μm in average diameter), and 0.7 g of ethylcellulose as a resin were mixed. Butylcarbidol as a solvent was added to the mixture until the viscosity of the resulting mixture became suitable for application. The mixture was milled to prepare a paste. To accelerate the solution of ethylcellulose as a resin binding agent, xylene, acetone or the like may be added to the mixture.

Then, the paste was applied both on the measurement-gas-side outer surface of the as-yet unsintered cylindrical solid-state electrolytic body and on the reference-gas-side inner surface thereof, and then sintered to prepare a sintered solid-state electrolytic body 41 and two electrode layers 43 and 44. Otherwise, the inner electrode layer 44 may be formed on the surface of the sintered solid-state electrolytic body by a known electroless method.

Further, plasma spraying of alumina-magnesia spinel powder onto the surface of the catalytic electrode layer 43 was carried out by a known method to form a porous protection layer 45 for protecting the electrode against the measurement gas. Thus, the element 1a was produced. The protection layer 45 can be formed at any time after the catalytic electrode layer 43 is formed.

The element according to Comparative Example 3 was produced in the same manner as described above, except that the metal powder other than a noble metal powder used in the paste was replaced by zirconium dioxide powder.

(2) Production of the Elements as related to Examples 4, 5 and 6 and Comparative Examples 4, 5 and 6

The element 1b according to each of Examples 4, 5 and 6 has a hollow cylindrical body 2 coated with a solid-state electrolytic layer 3, and a heating portion 8 constituted by an insulating layer formed by printing. A partly broken perspective view of the element is shown in FIG. 2. An exploded perspective view of the element is shown in FIG. 3.

In more detail, this element has the following configuration:

First and second reference electrodes 4 and 5 are provided on the inside surface of the solid-state electrolytic layer 3. First and second measurement electrodes 6 and 7 and the heating portion 8 are provided in the outside surface of the solid-state electrolytic layer 3. Four holes (from first to fourth) 9 to 12 are formed to communicate between the inside and outside of the hollow cylindrical body 2.

These holes 9 to 12 are arranged so that one pair of first and second holes 9 and 10 are opposite to the other pair of third and fourth holes 11 and 12. The first reference electrode 4 and the first measurement electrode 6 are respectively provided on the inner circumferential surface of the solid-state electrolytic layer 3 abutting the hollow cylindrical body 2 and the outer circumferential surface thereof, electrodes 4 and 6 being arranged in a position corresponding to the pair of first and second holes 9 and 10. Similarly, the second reference electrode 5 and the second measurement electrode 7 are arranged in a position corresponding to the other pair of third and fourth holes 11 and 12.

The first and second reference electrodes 4 and 5 are connected to a reference electrode terminal 14, as shown in FIG. 3, via a through-hole 21 provided in the solid-state electrolytic layer 3. The first and second measurement electrodes 6 and 7 are connected to a measurement electrode terminal 15. The heating portion 8 is connected to two heating terminals 16 and 17.

EXAMPLE 4

The method for producing this element was as follows. For convenience of explanation, sintered parts are identified by the same name and same reference numeral as unsintered parts.

Zirconia powder prepared so as to be partially stabilized by $Y_2O_3$ was mixed with organic resin, and a solid-state electrolytic green sheet 3a having a thickness of about 0.3 mm was formed therefrom using a doctor blade method. Then, Pt reference electrodes 4 and 5 and a lead portion were formed on a surface of the green sheet 3a by screen printing. Films serving as porous Pt measurement electrodes (catalytic electrodes) 6 and 7 after sintering were formed on the other surface of the green sheet 3a from the paste prepared in Example 1 in the same manner as described above.

Then, measurement electrode protection layers 22 and 23, an insulating layer 24 having window portions 26 and 27, a Pt heater having a heating portion 8 and lead-out portions 16 and 17, and an insulating layer 28 having window portions 30 and 31 were successively formed by screen printing.

Further, a lead portion 4, of the reference electrodes 4 and 5 was connected to the reference electrode terminal 14 via the through-hole 21 provided in the green sheet 3a. The upper surfaces of the terminal portions 14 and 15 of the electrodes and the upper surfaces of the terminal portions 16 and 17 of the heating matter were subjected to screen printing under the condition that the respective insulating layers 25 and 29 were removed.

The stratified assembly thus prepared was rolled on the hollow cylindrical body 2 and sintered to prepare an oxygen detection element 1b.

The element according to Comparative Example 4 was produced in the same manner as described above except that the zirconium butylate used in the paste was replaced by zirconium oxide powder.

EXAMPLE 5

The method for producing this element was as follows:

Zirconia powder prepared so as to be partially stabilized by $Y_2O_3$ was mixed with organic resin, and a solid-state electrolytic green sheet 3 having a thickness of about 0.3 mm was formed therefrom using a doctor blade method. Then, Pt reference electrodes 4 and 5 and a lead portion were formed on a surface of the green sheet 3 by screen printing. Films serving as porous Pt measurement electrodes (catalytic electrodes) 6 and 7 after sintering were formed on the other surface of the green sheet 3 from the paste prepared in Example 2 in the same manner as described above.

Then, measurement electrode protection layers 22 and 23, an insulating layer 24 having window portions 26 and 27, a Pt heater having a heating portion 8 and lead-out portions 16 and 17, and an insulating layer 28 having window portions 30 and 31 were successively formed by screen printing.

Further, a lead portion 4' of the reference electrodes 4 and 5 was connected to the reference electrode terminal 14 via the through-hole 21 provided in the green sheet 3. The upper surfaces of the terminal portions 14 and 15 of the electrodes and the upper surfaces of the terminal portions 16 and 17 of the heater were subjected to screen printing under the condition that the respective insulating layers 25 and 29 were removed.

The stratified assembly thus prepared was rolled on the hollow cylindrical body 2 and sintered to prepare an oxygen detection element 1b.

The element according to Comparative Example 5 was produced in the same manner as described above, except that the co-precipitated powder used in the paste was replaced by zirconium dioxide powder.

EXAMPLE 6

The method for producing this element was as follows:

Zirconia powder prepared so as to be partially stabilized by $Y_2O_3$ was mixed with organic resin, and a solid-state electrolytic green sheet 3 having a thickness of about 0.3 mm was formed therefrom using a doctor blade method. Then, Pt reference electrodes 4 and 5 and a leads portion were formed on a surface of the green sheet 3 by screen printing. Films serving as porous Pt measurement electrodes (catalytic electrodes) 6 and 7 after sintering were formed on the other surface of the green sheet 3 from the paste prepared in Example 3 in the same manner as described above.

Then, measurement electrode protection layers 22 and 23, an insulating layer 24 having window portions 26 and 27, a Pt heater having a heating portion 8 and lead-out portions 16 and 17, and an insulating layer 28 having window portions 30 and 31 were successively formed by screen printing.

Further, a lead portion 4' of the reference electrodes 4 and 5 was connected to the reference electrode terminal 14 via the through-hole 21 provided in the green sheet 3. The upper surfaces of the terminal portions 14 and 15 of the electrodes and the upper surfaces of the terminal portions 16 and 17 of the heater were subjected to screen printing under the condition that the respective insulating layers 25 and 29 were removed.

The stratified assembly thus prepared was rolled on the hollow cylindrical body 2 and sintered to prepare an oxygen detection element 1b.

The element according to comparative Example 6 was produced in the same manner as described above, except that the metal powder other than a noble metal powder used in the paste was replaced by zirconium oxide powder.

(3) Test of Examples 1 to 6 and Comparative Examples 1 to 6

Tests were performed on the oxygen detection elements described above. For these tests, the elements were each joined to a housing (not shown) and installed in an exhaust gas pipe of an automobile (not shown). To examine the toxic resistance of the elements, the amount ($\Delta A/F$) of change of a controlled air-fuel ratio was measured after the automobile was driven for 20 hours at a speed of 40 miles per hour with silicone oil added to the gasoline in an amount of 50 ppm.

The amount of change for each of the elements of Examples 1, 2 and 3 was not more than 0.02, the amount of change for each of the elements of Examples 4, 5 and 6 was not more than 0.01, the amount of change for each of the elements of Comparative Examples 1, 2 and 3 was 0.3, and the amount of change for each of the elements of Comparative Examples 4, 5 and 6 was 0.1.

That is, the amount of change for each of Examples 1 to 6 was not more than 0.02, whereas the amount of change for each of Comparative Examples 1 to 6 was 0.3 or 0.1. In short, the amount of change for each of the Examples of the invention was about one-tenth that for each of comparative Examples. This shows that the toxic resistance in each of the Examples of the invention is very good. In particular, the performance for each of Examples 4 to 6 is excellent. This is because the heating portion and the like are sintered together as one body.

The elements of Examples 4 to 6 also have the following effects. Because one pair of electrodes, that is, the first reference electrode 4 and the first measurement electrode 6, are formed so as to be located opposite to the other pair, that is, the one reference electrode 5 and the second measurement electrode 7, the influence of the flow of the measurement gas on the output of the element 1b is reduced so that high performance can be maintained, even in the case where the position of the element 1b is different. Further, because the two pairs of electrodes are arranged so as to be opposite to each other, that is, at an angle of 180 degrees, the partial pressure of oxygen can be measured with accuracy, even in the case where the flow of measurement gas is not perpendicular to the plane of the electrodes. Although the embodiment corresponds to the case where two pairs of electrodes are provided, the present invention is not limited to this specific embodiment. For example, in the case where three pairs of electrodes are provided, they can be arranged at equal intervals of 120 degrees, and in the case where four pairs of electrodes are provided, they can be arranged at equal intervals of 90 degrees. In these cases, the directivity of the element can be further reduced. Further, because the element is cylindrical and has a thin and hollow cylindrical body provided with a hollow portion at the center, the heat capacity of the element is so little that the heat efficiency of the heater can be improved. Accordingly, the consumption of electric power can be reduced. Furthermore, because the heater and the like are formed on the green sheet by thick-film printing, the element can be produced very easily.

It is to be understood that the present invention is not limited to the aforementioned specific embodiment and that various changes and modifications may be made corresponding to the application at hand without departing from the scope of the present invention. For example, factors such as form, size and the like of the solid-state electrolytic body, factors such as thickness, position, porosity, degree of coating of the solid-state electrolytic body, material, proportion of noble metal and ceramics, and the like of the catalytic electrode layer, and factors such as material, form, thickness, and the like of the inner electrode layer, and factors such as material porosity, thickness, position, degree of coating of the catalytic electrode layer and the like of the electrode protection layer can be selected suitably for the particular application. Further, in the case where a relatively thin layer is used as the solid-state electrolytic body, factors such as form, size, thickness and the like of the support can also be suitably selected.

Because a paste containing an organic metal compound is used in the method of the present invention, the organic metal compound is dispersed more uniformly with respect to noble metal powder when the paste is applied onto the solid-state electrolytic body compared with the conventional case where a fine ceramic powder is used. When the applied paste is subjected to heat decomposition in the sintering step, the organic metal compound can be subjected to heat decomposition before the sintering of the noble metal powder starts. Accordingly, the matter produced by heat decomposition of the organic metal compound can surround the noble metal powder so that self sintering of the noble metal powder can be prevented.

Further, because paste containing co-precipitated powder of a noble metal and metal hydroxide co-precipitated from a uniform solution is used in the method of the present invention, the metal hydroxide is dispersed more uniformly with respect to the noble metal powder when the paste is applied onto the solid-state electrolytic body compared with the conventional case where fine-powder-like ceramic powder is used. When the applied paste is subjected to heat decomposition in the sintering process, the metal hydroxide can be subjected to heat decomposition before sintering of the noble metal powder. Accordingly, the matter produced by heat decomposition of the metal hydroxide can surround the noble metal powder so that self sintering of the noble metal powder can be prevented.

Further, paste containing two similar kinds of powder, that is, a noble metal powder and a metal powder similar in properties to noble metal but not a noble metal, is used in the producing method of the present invention. Accordingly, the metal powder serving as an oxide after heating is dispersed more uniformly with respect to the noble metal powder when the paste is applied onto the solid-state electrolytic body compared with the conventional case where different kinds of powder, that is, noble metal powder and ceramic powder, are used. Moreover, according to the present invention, the paste can be made uniform very easily with perfect dispersion of the metal powder, compared with the conventional case where the dispersion of the ceramic powder may be insufficient because of the alkalinity of the ceramic powder depending upon the kind of solvent used. Furthermore, when the applied paste is subjected to heat decomposition in the sintering process, the metal powder can be decomposed by an oxidation reaction before sintering of the precious metal powder. Accordingly, the matter produced by heat decomposition of the metal powder can surround the noble metal powder so that the self sintering of the noble metal powder can be prevented.

Consequently, according to the present invention, electrodes having uniform pores can be formed efficiently and easily. Accordingly, very few large pores are formed, so that very little toxic matter in the measurement gas can reach the three-phase boundary directly and, accordingly, the present of toxic matter will not result in abnormalities in the characteristics of the device after a short exposure time. Accordingly, this element is very excellent in durability against toxic matter.

There is no necessity of adding a large amount of metal oxide material (metal powder to be changed to metal oxide) to the catalytic material as in the prior art. Accordingly, the conductive resistance of the electrode can be reduced and, at the same time, the contact area between the solid-state electrolyte and the catalytic material as an electrode on the surface of the solid-state electrolytic body can be increased compared with the prior art.

As described above, according to the present invention, an element excellent in durability against toxic matter and capable of detecting oxygen efficiently and accurately can be produced.

What is claimed is:

1. A method for producing an oxygen detection element, comprising:
    a first step of applying a paste to be sintered to form a catalytic electrode layer onto at least a part of an oxygen-ion conductive solid-state electrolytic body, said paste mainly containing noble metal powder acting as a catalyst and an organic metal compound, and sintering said paste, so as to subject said organic metal compound to heat decomposition prior to a start of sintering of said noble metal powder so that matter produced by heat decomposition of said organic metal compound surrounds said noble metal powder to prevent said noble metal powder from self-sintering, to thereby form said catalytic electrode layer at a predetermined position on said surface of said solid-state electrolytic body after sintering; and
    a second step of forming an electrode protection layer for coating and protecting at least a part of said catalytic electrode layer.

2. The method for producing an oxygen detection element of claim 1, wherein said oxygen-ion conductive solid-state body is sintered prior to said first step.

3. The method for producing an oxygen detection element of claim 1, wherein said oxygen ion conductive solid-state body is previously unsintered and is sintered during said first step.

4. The method for producing an oxygen detection element of claim 1, wherein said second step of forming said electrode protection layer is performed after said first step.

5. The method for producing an oxygen detection element of claim 1, wherein said second step of forming said electrode protection layer is performed simultaneously with said first step.

6. The method for producing an oxygen detection element of claim 1, wherein said organic metal compound consists of a metal alkoxide.

7. The method for producing an oxygen detection element of claim 1, wherein said organic metal compound contains an alkyl group and a butyl group, a proportion of said alkyl group being larger than a proportion of said butyl group.

8. The method for producing an oxygen detection element of claim 7, wherein said organic metal compound is in solution.

9. The method for producing an oxygen detection element of claim 1, wherein a metal of said organic metal compound is selected from the group consisting of Li, Na, K, Be, Mg, Ca, Sr, B, Al, Ga, Si, Ge Sb, Bi, Ti, Zr, V and Y.

10. The method for producing an oxygen detection element of claim 1, wherein a metal of said organic metal compound is selected from the group consisting of Mg, Al, Zr, Ca, Sr, Ti and Y.

11. The method for producing an oxygen detection element of claim 1, wherein said noble metal consists of at least one metal selected from the group consisting of Ag, Au, Ru, Os, Rh, Ir, Pd and Pt.

12. The method for producing an oxygen detection element of claim 1, wherein said electrode layer formed from said paste contains platinum and a ceramic component in an amount of 0.5 to 30 mol % relative to said platinum.

13. The method for producing an oxygen detection element of claim 1, wherein said electrode layer formed from said paste contains platinum and a ceramic component in an amount of 1.5 to 7.5 mol % relative to said platinum.

14. The method for producing an oxygen detection element of claim 1, wherein said protection layer is made of spinel of alumina-magnesia.

15. The method for producing an oxygen detection element of claim 1, wherein said solid-state electrolytic body is made of zirconia partially stabilized by $Y_2O_3$.

16. A method for producing an oxygen detection element, comprising:

a first step of applying a paste to be sintered to form a catalytic electrode layer onto at least a part of an oxygen-ion conductive solid-state electrolytic body, said paste mainly containing co-precipitated powder consisting of noble metal and metal hydroxide, said metal hydroxide being a compound other than a noble metal element compound, and sintering said paste, so as to subject said metal hydroxide to heat decomposition prior to a start of sintering of said noble metal powder so that matter produced by heat decomposition of said metal hydroxide surrounds said noble metal powder to prevent said noble metal powder from self-sintering, to thereby form said catalytic electrode layer at a predetermined position on said surface of said solid-state electrolytic body after sintering; and a second step of forming an electrode protection layer for coating and protecting at least a part of said catalytic electrode layer.

17. The method for producing an oxygen detection element of claim 16, wherein said oxygen-ion conductive solid-state body is sintered prior to said first step.

18. The method for producing an oxygen detection element of claim 16, wherein said oxygen ion conductive solid-state body is previously unsintered and is sintered during said first step.

19. The method for producing an oxygen detection element of claim 16, wherein said second step of forming said electrode protection layer is performed after said first step.

20. The method for producing an oxygen detection element of claim 16, wherein said second step of forming said electrode protection layer is performed simultaneously with said first step.

21. The method for producing an oxygen detection element of claim 16, wherein a metal of said metal hydroxide is selected from the group consisting of Li, Na, K, Be, Mg, Ca, Sr, B, Al, Ga, Si, Ge Sb, Bi, Ti, Zr, V and Y.

22. The method for producing an oxygen detection element of claim 16, wherein a metal of said metal hydroxide is selected from the group consisting of Mg, Al, Zr, Ca, Sr, Ti and Y.

23. The method for producing an oxygen detection element of claim 16, wherein said noble metal consists of at least one metal selected from the group consisting of Ag, Au, Ru, Os, Rh, Ir, Pd and Pt.

24. The method for producing an oxygen detection element of claim 16, wherein said electrode layer formed from said paste contains platinum and a ceramic component in an amount of 0.5 to 30 mol % relative to said platinum.

25. The method for producing an oxygen detection element of claim 16, wherein said electrode layer formed from said paste contains platinum and a ceramic component in an amount of 1.5 to 7.5 mol % relative to said platinum.

26. The method for producing an oxygen detection element of claim 16, wherein said protection layer is made of spinel of alumina-magnesia.

27. The method for producing an oxygen detection element of claim 16, wherein said solid-state electrolytic body is made of zirconia partially stabilized by $Y_2O_3$.

28. A method for producing an oxygen detection element, comprising:

a first step of applying a paste to be sintered to form a catalytic electrode layer onto at least a part of an oxygen-ion conductive solid-state electrolytic body, said paste mainly containing noble metal powder and a powder of a metal, other than a noble metal, having properties similar to those of said noble metal, and sintering said paste, so as to oxidize said metal other than a noble metal prior to a start of sintering of said noble metal so that matter produced by oxidation of said powder of a metal other than a noble metal surrounds said noble metal powder to prevent said noble metal powder from self-sintering, to thereby form said catalytic electrode layer at a predetermined position on said surface of said solid-state electrolytic body after sintering; and a second step of forming an electrode protection layer for coating and protecting at least a part of said catalytic electrode layer.

29. The method for producing an oxygen detection element of claim 28, wherein said oxygen-ion conductive solid-state body is sintered prior to said first step.

30. The method for producing an oxygen detection element of claim 28, wherein said oxygen ion conductive solid-state body is previously unsintered and is sintered during said first step.

31. The method for producing an oxygen detection element of claim 28, wherein said second step of forming said electrode protection layer is performed after said first step.

32. The method for producing an oxygen detection element of claim 28, wherein said second step of forming said electrode protection layer is performed simultaneously with said first step.

33. The method for producing an oxygen detection element of claim 28, wherein said metal other than noble metal is selected from the group consisting of Li, Na, K, Be, Mg, Ca, Sr, B, Al, Ga, Si, Ge Sb, Bi, Ti, Zr, V and Y.

34. The method for producing an oxygen detection element of claim 28, wherein said metal other than noble metal is selected from the group consisting of Mg, Al, Zr, Ca, Sr, Ti and Y.

35. The method for producing an oxygen detection element of claim 28, wherein said noble metal consists of at least one a metal selected from the group consisting of Ag, Au, Ru, Os, Rh, Ir, Pd and Pt.

36. The method for producing an oxygen detection element of claim 28, wherein said electrode layer formed from said paste contains platinum and a ceramic component in an amount of 0.5 to 30 mol % relative to said platinum.

37. The method for producing an oxygen detection element of claim 28, wherein said electrode layer formed from said paste contains platinum and a ceramic component in an amount of 1.5 to 7.5 mol % relative to said platinum.

38. The method for producing an oxygen detection element of claim 28, wherein said protection layer is made of spinel of alumina-magnesia.

39. The method for producing an oxygen detection element of claim 28, wherein said solid-state electrolytic body is made of zirconia partially stabilized by $Y_2O_3$.

* * * * *